(12) United States Patent
Schoening et al.

(10) Patent No.: US 10,196,334 B2
(45) Date of Patent: Feb. 5, 2019

(54) PROCESS FOR THE ALKYLATION OF PHENOLS

(71) Applicant: BASF SE, Ludwigshafen am Rhein (DE)

(72) Inventors: Kai-Uwe Schoening, Oberwil (CH); Walid A. Al-Akhdar, Cary, NC (US); Tiziano Nocentini, Birsfelden (CH); Gerard Vilain, Breisach (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 15/758,010

(22) PCT Filed: Sep. 7, 2016

(86) PCT No.: PCT/EP2016/071012
§ 371 (c)(1),
(2) Date: Mar. 7, 2018

(87) PCT Pub. No.: WO2017/042181
PCT Pub. Date: Mar. 16, 2017

(65) Prior Publication Data
US 2018/0244595 A1    Aug. 30, 2018

(30) Foreign Application Priority Data

Sep. 11, 2015 (EP) .................................... 15184850

(51) Int. Cl.
*C07C 37/14* (2006.01)
*B01J 31/00* (2006.01)
*B01J 31/22* (2006.01)

(52) U.S. Cl.
CPC .............. *C07C 37/14* (2013.01); *B01J 31/00* (2013.01); *B01J 31/2226* (2013.01)

(58) Field of Classification Search
CPC ......... C07C 39/15; C07C 37/11; C07C 37/50; C07C 37/74; C07C 39/06; C07C 37/00

USPC ......................... 568/730, 749, 756, 789, 805
See application file for complete search history.

(56) References Cited

U.S. PATENT DOCUMENTS

| 2,353,282 A | 7/1944 | Turkington et al. |
| 3,751,509 A | 8/1973 | Grigorievich Liakumovich |
| 3,970,708 A | 7/1976 | Katsumoto |
| 4,260,833 A | 4/1981 | Firth |
| 2013/0150629 A1 | 6/2013 | D'Souza et al. |

FOREIGN PATENT DOCUMENTS

| CN | 1935763 | 3/2007 | |
| CS | 276820 | 3/1992 | |
| GB | 1062298 | 3/1967 | |
| GB | 1338709 | 11/1973 | |
| JP | 60-255742 | 12/1985 | |
| JP | 63-165337 | 7/1988 | |
| WO | 2011/069052 A2 | 6/2011 | |
| WO | WO-2011069052 A2 * | 6/2011 | ............. C07C 37/14 |

OTHER PUBLICATIONS

International Search Report dated Dec. 21, 2016, in PCT/EP2016/071012, filed Sep. 7, 2016.
European Search Report dated Feb. 17, 2016 in European Patent Application No. 15 18 4850.

* cited by examiner

*Primary Examiner* — Deborah D Carr
(74) *Attorney, Agent, or Firm* — Oblon, McClelland, Maier & Neustadt, L.L.P.

(57) ABSTRACT

The present invention relates to a process for the preparation of 2,6-di-tert-butyl phenol by reacting phenol with isobutylene in presence of an aluminum phenoxide catalyst, comprising i) preparing an aluminum phenoxide catalyst and phenol comprising mixture a) by mix-ing aluminum metal with phenol, and activating the catalyst by heating the mixture to a temperature of 100 to 180° C., and ii) carrying out a reaction b) by reacting mixture a) with an isobutylene comprising stream comprising 20 to 90% by weight of isobutylene and 10 to 80% by weight of 1-butene and/or 2-butene, which reaction is carried out under pressure and the maximum pressure is 5 to 20 bar.

10 Claims, No Drawings

PROCESS FOR THE ALKYLATION OF PHENOLS

The present invention relates to a process for the preparation of 2,6-di-tert-butyl phenol by reacting phenol with an isobutylene comprising stream, which stream additionally comprises higher amounts of 1-butene and/or 2-butene, in presence of an aluminum phenoxide catalyst.

2,6-di-tert-butyl phenol is used industrially as UV stabilizer and antioxidant for hydrocarbon-based products ranging from petrochemicals to plastics, and also as a starting material for the preparation of various antioxidants for plastics, like Irganox® 1010 or Irganox® 1076.

The preparation of 2,6-di-tert-butyl phenol usually results in the formation of undesired by-products, like 2-tert-butyl phenol, 2,4-di-tert-butyl phenol, 2,5-di-tert-butyl phenol and 2,4,6-tri-tert-butyl phenol and there is still a need to selectively react isobutylene with phenol in order to reduce the formation of such by-products and to produce 2,6-ditert-butyl phenol in high yields.

In addition, isobutylene comprising streams usually also comprise 1-butene and/or 2-butene which, when reacted with phenol, lead to the formation of the undesired by-product 2-sec-butyl-6-tert-butyl phenol.

WO-A-2011/069052 discloses a process for the preparation of 2,6-di-tert-butyl phenol by reacting phenol with an isobutylene stream, containing low amounts of 1-butene and/or 2-butene.

However, common isobutylene streams from olefin steam crackers or refineries usually contain higher amounts of 1-butene and/or 2-butene. For such streams the higher amount of 1-butene and/or 2-butene may lead to the formation of higher amounts of the undesired by-product 2-sec-butyl-6-tert-butyl phenol.

Therefore, there is still a need for a process for the preparation of 2,6-di-tert-butyl phenol, wherein also common isobutylene streams can be used and which result in low amounts of by-products and high yields of 2,6-di-tert-butyl phenol.

Accordingly, the present invention relates to a process for the preparation of 2,6-di-tert-butyl phenol by reacting phenol with isobutylene in presence of an aluminum phenoxide catalyst, comprising i) preparing an aluminum phenoxide catalyst and phenol comprising mixture a) by mixing aluminum metal with phenol, and activating the catalyst by heating the mixture to a temperature of 100 to 180° C., and ii) carrying out a reaction b) by reacting mixture a) with an isobutylene comprising stream comprising 20 to 90% by weight of isobutylene and 10 to 80% by weight of 1-butene and/or 2-butene, which reaction is carried out under pressure and the maximum pressure is 5 to 20 bar.

Here and in the following the amounts of components of the isobutylene comprising stream are given in percent by weight, based on the total weight of the stream.

The aluminum phenoxide catalyst of mixture a) has at least one phenoxy group bonded to aluminum, aluminum triphenoxide being preferred.

For the preparation of mixture a) it is has been proven advantageous to remove air from the reactor before the addition of phenol and aluminum. In a preferred embodiment this is effected by purging the reactor with nitrogen.

Preparation of the aluminum phenoxide catalyst of mixture a) is preferably carried out at a temperature of 120 to 180° C., more preferably 140 to 180° C. and especially 150 to 170° C. The preparation is preferably carried out under pressure, like a pressure of 5 to 20 bar, especially 10 to 20 bar.

The molar ratio of phenol per mole of aluminum in mixture a) is preferably 10:1 to 500:1, especially 20:1 to 300:1 and more preferably 50:1 to 200:1.

In general, mixture a) can be used as such for the further reaction with the isobutylene comprising stream.

The isobutylene comprising stream preferably comprises 20 to 80%, more preferably 20 to 70% and especially 20 to 60% by weight of isobutylene. The amount of 1-butene and/or 2-butene in the stream is preferably 15 to 60%, more preferably 15 to 50% and especially 15 to 40% by weight.

Interesting isobutylene comprising streams comprise 20 to 80% by weight of isobutylene and 15 to 60%, more preferably 15 to 50% and especially 15 to 40% by weight of 1-butene and/or 2-butene. Highly preferred are isobutylene comprising streams comprising 20 to 70% by weight of isobutylene and 15 to 60%, more preferably 15 to 50% and especially 15 to 40% by weight of 1-butene and/or 2-butene. Most preferred are isobutylene comprising streams comprising 20 to 60% by weight of isobutylene and 15 to 60%, more preferably 15 to 50% and especially 15 to 40% by weight of 1-butene and/or 2-butene.

It is to be understood that the sum of the amounts of the components of the isobutylene comprising streams (like isobutylene and 1-butene and/or 2-butene) does not exceed 100% by weight.

The source of such isobutylene comprising streams can vary. For example, the isobutylene comprising stream can be a discharge stream from a fluid catalytic cracking (FCC) unit. FCC is an important conversion process used in petroleum refineries. An example of a further source is a thermal cracking unit, like a steam cracking unit, according to which saturated hydrocarbons are broken down into smaller, often unsaturated, hydrocarbons. Typically, the corresponding C4 fractions are used, which are mixtures of hydrocarbons with prevailing content of 4 carbon atoms in their molecules. In general, such C4 fractions comprise isobutylene, 1-butene, 2-butene, butane (as n-butane or isobutane). A typical amount for the sum of n-butane and isobutane is 5 to 30% by weight.

Usually corresponding raffinate-I is used, which is the C4 fraction after butadiene extraction. In general, it is preferred to use C4 fractions after butadiene extraction.

The molar ratio of isobutylene to phenol is preferably 1.9 to 2.6, especially 2.0 to 2.4.

It is preferred to carry out the reaction of mixture a) with an isobutylene comprising stream at a temperature of 90 to 140° C., especially 90 to 125° C.

The reaction is carried out under pressure. The maximum pressure is preferably 10 to 20 bar.

Usually, the reactor is closed and feeding of the isobutylene comprising stream results in an increase of the pressure. The maximum pressure is normally reached after the isobutylene comprising stream has been fed and the temperature is held at the reaction temperature (being normally the maximum temperature during reaction). Thereafter, due to consumption of isobutylene during the reaction, the pressure decreases again.

It is preferred to feed the isobutylene comprising stream continuously.

In the course of the reaction of mixture a) with an isobutylene comprising stream it is also possible to release at least one time the pressure and remove unreacted stream. In such case, the isobutylene comprising stream is fed before and after release of the pressure. A process, wherein during reaction b) at least one time the pressure is released and unreacted stream is removed, is therefore preferred.

According to a preferred embodiment of the present invention the isobutylene comprising stream is fed continuously, which feeding is at least one time, preferably one to three times and most preferably one time, interrupted by releasing the pressure and removing unreacted stream.

If desired, the aluminum phenoxide catalyst may be removed at the end of the reaction. For example, aqueous sulfuric acid may be added to remove the aluminum (as inorganic aluminum compounds) in the aqueous phase. For this purpose, aqueous sulfuric acid is added and the aqueous phase is removed, which procedure may be repeated two to three times. Then, in general, the product is neutralized, for example by addition of an aqueous sodium carbonate solution, and the aqueous phase is removed again.

2,6-di-tert-butyl phenol is used industrially as UV stabilizer and antioxidant for hydrocarbon-based products ranging from petrochemicals to plastics. 2,6-Di-tert-butylphenol is likewise a precursor for the preparation of antioxidants and light-protection agents for plastics. Representative examples thereof include 3,5-di-tert-butyl-4-hydroxybenzyl chloride (CAS number 955-01-1), 3,5-di-tert-butyl-4-hydroxybenzyl alcohol (CAS number 88-26-6), methyl-3-(3,5-di-tert-butyl-4-hydroxyphenyl)-propionate (CAS number 6386-38-5), pentaerythritol tetrakis(3-(3,5-di-tert-butyl-4-hydroxyphenyl)propionate) (CAS number 6683-19-8) and octadecyl-3-(3,5-di-tert.butyl-4-hydroxyphenyl)-propionate (CAS number 2082-79-3).

The process according to the present invention allows the preparation of 2,6-di-tert-butyl phenol in high yields and with low amounts of by-products. Commonly used isobutylene streams, like raffinate-1 streams of C4 fractions, usually comprise a higher amount of 1-butene and/or 2-butene (like amounts of 15 to 60% of 1-butene and/or 2-butene). It is well known that such butenes react with phenol to the undesired by-product 2-sec-butyl-6-tert-butyl phenol. Due to the high amount of 1-butene and/or 2-butene in the isobutylene comprising stream, it would have been expected that as a result also a high amount of such 2-sec-butyl-6-tert-butyl phenol by-product would have been formed. However, according to the process of the present invention also the amount of this by-product is kept at low levels, which allows the use of common isobutylene streams, for example those which are obtained as C4 fraction from naphtha steam cracking as raffinate-1 after butadiene extraction.

The following Example illustrates the invention:

EXAMPLE a) Preparation of Aluminum Phenoxide Catalyst and Phenol Containing Mixture Air from an autoclave is removed by flushing with nitrogen. 129 g of phenol as crystals are added to the inertised reactor together with 0.38 g of aluminum. The reactor is closed and the mass is heated under stirring up to 160° C. within 25 minutes. Once the target temperature is reached, the final pressure is normally 14.5 to 15.5 bar. These conditions are kept for 30 minutes, and then the gas is removed from the autoclave until an inner pressure (Pi) of 2 to 3 bar is reached. The reaction mass is cooled down to 90° C. within 30 minutes. Once the target temperature is reached, the residual pressure is released.

b) Reaction of the Mixture Prepared According to a) with an Isobutylene Comprising Stream The mixture prepared according to a) is reacted with a stream comprising 78.5% isobutylene, 15% 1-butene, and 6.5% isobutane (each in percent by weight, based on the total weight of the stream).

The initial reaction temperature is 90° C. The stream is charged into the reactor at the rate of 4 g/minute for the first thirty two minutes (first addition of reactant gas).

Temperature is raised to 121° C. at the rate of 1.1° C./minute after 20 minutes of stream addition. Once the temperature is reached the pressure is about 15 bar.

The temperature is held steady at 121° C. for 65 minutes before cooling the reaction mass to 90° C. at the rate of 1° C./minute. In the course of holding the reaction mass at the temperature of 121° C. the pressure drops down to 9 bar.

The stream is then added at the start of the cool down period at the rate of 4 g/minute for 20 minutes (second addition of reactant gas). During the second addition of reactant gas, the pressure reaches again about 15 bar and at the end of cooling it is dropped down to 9 bar.

The temperature is held at 90° C. for the remainder of the reaction in which the pressure drops down to about 7 bar.

The total reaction time is 5 hours. The molar ratio of isobutylene to phenol is 2.12.

Comparative Example

The procedure of the above Example is followed exactly, but using a stream comprising 78.5% isobutylene, 1.1% 1-butene and 20.4% isobutane (each in percent by weight, based on the total weight of the stream).

Results

|  | Example | Comparative Example |
|---|---|---|
| 2,6-di-tert-butyl phenol | 85.0% | 73.6% |
| Unreacted phenol | 0.0% | 0.5% |
| By-product 2-tert-butyl phenol | 3.7% | 15.8% |
| By-product 2,4-di-tert-butyl phenol | 0.4% | 1% |
| By-product 2,5-di-tert-butyl phenol | 0.1% | 0.3% |
| By-product 2,4,6-tri-tert-butyl phenol | 10.0% | 7.8% |
| By-product 2-sec-butyl-6-tert-butyl phenol | 0.2% | 0% |
| Sum of by-products | 14.4% | 24.9% |

All amounts indicated in the above Table are given in percent by weight, based on the weight of the crude product obtained according to the respective example.

The amount of 2-sec-6-tert-butyl phenol in the Example according to the present invention is 0.2%, representing the reaction of 0.4% of the 1-butene in the initial stream.

The invention claimed is:

1. A process for the preparation of 2,6-di-tert-butyl phenol by reacting phenol with isobutylene in presence of an aluminum phenoxide catalyst, the method comprising:
i) preparing an aluminum phenoxide catalyst and phenol comprising mixture a) by mixing aluminum metal with phenol, and activating the catalyst by heating the mixture to a temperature of 100 to 180° C., and
ii) carrying out a reaction b) by reacting mixture a) with an isobutylene-comprising stream comprising 20 to 90% by weight of isobutylene and 10 to 80% by weight of 1-butene and/or 2-butene, wherein the reaction is carried out under pressure and the maximum pressure is 5 to 20 bar.

2. The process according to claim 1, wherein the activation of the catalyst of mixture a) is carried out at a temperature of 120 to 180° C.

3. The process according to claim 1, wherein reaction b) is carried out at a temperature of 90 to 140° C.

4. The process according to claim 1, wherein for reaction b) a molar ratio of isobutylene to phenol is 1.9 to 2.6.

5. The process according to claim 1, wherein in reaction b) the maximum pressure is 10 to 20 bar.

6. The process according to claim 1, wherein the amount of isobutylene in the stream is 20 to 70% by weight.

7. The process according to claim 1, wherein the amount of isobutylene in the stream is 20 to 60% by weight.

8. The process according to claim 1, wherein the amount of 1-butene and 2-butene in the stream is 15 to 60% by weight.

9. The process according to claim 1, wherein during reaction b) at least one time the pressure is released and unreacted stream is removed.

10. The process according to claim 9, wherein during reaction b) the stream is fed continuously, wherein the feeding is at least one time interrupted by releasing the pressure and removing unreacted stream.

* * * * *

UNITED STATES PATENT AND TRADEMARK OFFICE
CERTIFICATE OF CORRECTION

PATENT NO. : 10,196,334 B2  
APPLICATION NO. : 15/758010  
DATED : February 5, 2019  
INVENTOR(S) : Kai-Uwe Schoening et al.

Page 1 of 1

It is certified that error appears in the above-identified patent and that said Letters Patent is hereby corrected as shown below:

On the Title Page

In Column 2, item (57), Abstract, Line 5, delete "mix-ing" and insert -- mixing --, therefor.

Signed and Sealed this  
Twenty-first Day of April, 2020

Andrei Iancu  
*Director of the United States Patent and Trademark Office*